United States Patent
Notcovich et al.

(10) Patent No.: US 8,105,845 B2
(45) Date of Patent: Jan. 31, 2012

(54) SYSTEM AND METHOD FOR CARRYING OUT MULTIPLE BINDING REACTIONS IN AN ARRAY FORMAT

(75) Inventors: Ariel Notcovich, Haifa (IL); Alon Herschhorn, Nesher (IL); Shai Nimri, Kibbutz Sarid (IL); John Barich, Pleasant Hill, CA (US); Ariel Lipson, Haifa (IL); Ran Boaz, Haifa (IL); Doron Lipson, Tel Aviv (IL); Yaakov Levie, Misgav (IL)

(73) Assignee: Bio-Rad Haifa Ltd., Technion, Haifa (IL)

( * ) Notice: Subject to any disclaimer, the term of this patent is extended or adjusted under 35 U.S.C. 154(b) by 0 days.

(21) Appl. No.: 10/578,860

(22) PCT Filed: Nov. 14, 2004

(86) PCT No.: PCT/IL2004/001043
§ 371 (c)(1),
(2), (4) Date: Jun. 30, 2006

(87) PCT Pub. No.: WO2005/046859
PCT Pub. Date: May 26, 2005

(65) Prior Publication Data
US 2007/0087348 A1  Apr. 19, 2007

Related U.S. Application Data

(60) Provisional application No. 60/518,878, filed on Nov. 12, 2003.

(51) Int. Cl.
*G01N 33/543* (2006.01)
(52) U.S. Cl. .................................................. 436/518
(58) Field of Classification Search .............. 436/518, 436/514, 517; 435/4, 7.1, 287.1–287.3; 422/50
See application file for complete search history.

(56) References Cited

U.S. PATENT DOCUMENTS

| | | | |
|---|---|---|---|
| 5,384,261 A * | 1/1995 | Winkler et al. | 506/18 |
| 5,429,807 A | 7/1995 | Matson et al. | |
| 5,541,113 A * | 7/1996 | Siddigi et al. | 436/56 |
| 5,624,845 A | 4/1997 | Wickramasinghe et al. | |
| 6,110,707 A * | 8/2000 | Newgard et al. | 435/69.4 |
| 6,200,814 B1 * | 3/2001 | Malmqvist et al. | 436/52 |
| 6,268,141 B1 | 7/2001 | Matson et al. | |
| 6,478,839 B1 * | 11/2002 | Kansa et al. | 75/10.14 |
| 6,493,097 B1 * | 12/2002 | Ivarsson | 356/630 |
| 6,498,010 B1 | 12/2002 | Fitzgerald et al. | |
| 2001/0024788 A1 | 9/2001 | Hashimoto | |
| 2001/0040679 A1 | 11/2001 | Kawabata et al. | |
| 2002/0048792 A1 * | 4/2002 | Natesan et al. | 435/69.1 |
| 2003/0128043 A1 | 7/2003 | Zeltz et al. | |
| 2003/0198967 A1 | 10/2003 | Matson et al. | |
| 2005/0014179 A1 * | 1/2005 | Karlsson et al. | 435/6 |
| 2006/0210984 A1 * | 9/2006 | Lambert | 435/6 |

FOREIGN PATENT DOCUMENTS

| | | |
|---|---|---|
| JP | 8-256755 A | 10/1996 |
| JP | 11-344437 A | 12/1999 |
| JP | 2001-330608 A | 11/2001 |
| JP | 2002-509248 A | 3/2002 |
| JP | 2003-9859 A | 1/2003 |
| WO | 99/36766 A1 | 7/1999 |
| WO | 02/055993 A2 | 7/2002 |
| WO | 03/056296 A2 | 7/2003 |
| WO | 03/065041 A1 | 8/2003 |

OTHER PUBLICATIONS

XP-002319706: Karlsson, R., et al., "Surface Plasmon Resonance Detection and Multispot Sensing for Direct Monitoring of Interactions involving Low-Molecular-Weight Analytes and for Determination of Low Affinities", *Analytical Biochemistry*, pp. 274-280, (1995).
XP 000265940: Lofas, S., et al., "Bioanalysis with surface Plasmon Resonance", *Sensors and Actuators*, pp. 79-84, (1991).
Berger, C.E.H., et al., "Surface Plasmon Resonance Multisensing", Anal. Chem., pp. 703-706, (1998).

* cited by examiner

*Primary Examiner* — Ann Lam
(74) *Attorney, Agent, or Firm* — The Nath Law Group; Susanne M. Hopkins; Ari G. Zytcer

(57) ABSTRACT

A method for determining one or more kinetic parameters of binding between a first binding member and a second binding member. The method comprises adsorbing the first binding member to a surface at a plurality of microspots. The second binding member is then presented to the first binding member at each of the microspots, there being a plurality of combinations of first binding member surface density and second binding member concentration among the plurality of microspots. Data indicative of a binding reaction between the first of microspots are then obtained and analyzed so as to obtain one or more kinetic parameters of the binding between the first and second binding members. The invention also provides a system for carrying out the method. A method for localizing a molecular species at microspots on a surface, and a probe array produced by the method are also provided.

16 Claims, 11 Drawing Sheets

Ligand 1
$k_a = 2.52 \times 10^6$ 1/MS   $k_d = 3.24 \times 10^{-4}$ 1/s   $Chi^2 = 5.65$ Ligand 2
$k_a = 2.51 \times 10^6$ 1/MS   $k_d = 3.7 \times 10^{-4}$ 1/s   $Chi^2 = 7.85$ Ligand 3
$k_a = 3.06 \times 10^6$ 1/MS   $k_d = 3.82 \times 10^{-4}$ 1/s   $Chi^2 = 9.71$ Ligand 4

$k_a = 2.4 \times 10^6$ 1/MS  $k_d = 2.68 \times 10^{-4}$ 1/s  $Chi^2 = 11.8$

Ligand 5

$k_a = 8.98 \times 10^5$ 1/MS  $k_d = 2.5 \times 10^{-4}$ 1/s  $Chi^2 = 14.6$

Ligand 6

$k_a = 1.46 \times 10^6$ 1/MS  $k_d = 2.12 \times 10^{-4}$ 1/s  $Chi^2 = 7.54$

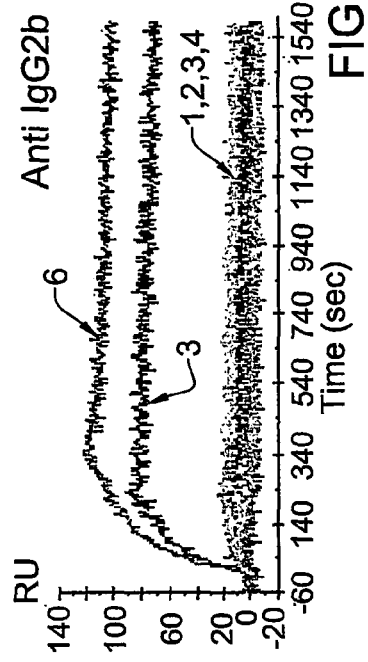
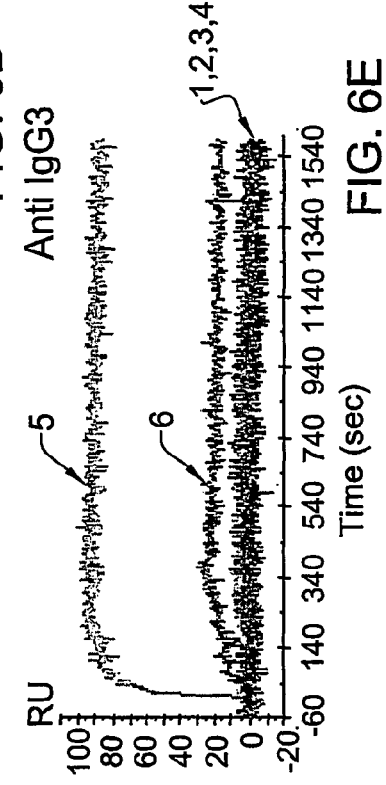
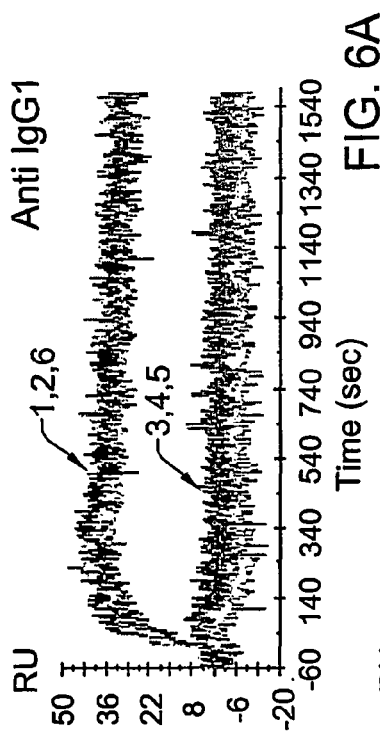
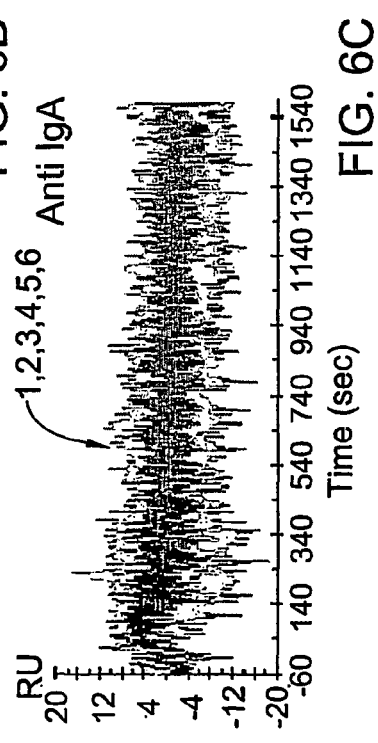
FIG. 6A Anti IgG1
FIG. 6B Anti IgG2b
FIG. 6C Anti IgA
FIG. 6D Anti IgG2b
FIG. 6E Anti IgG3
1 - IgG1(anti Il-2)
2 - IgG1(anti IL-4)
3 - IgG2a
4 - IgG2b
5 - IgG3
6 - IgG polyclonal

SYSTEM AND METHOD FOR CARRYING OUT MULTIPLE BINDING REACTIONS IN AN ARRAY FORMAT

This is a National Phase Application filed under 35 U.S.C. 371 as a national stage of PCT/IL2004/001043, filed Nov. 14, 2004, an application claiming the benefit under 35 U.S.C. 119(e) U.S. Provisional Application No. 60/518,878, filed Nov. 12, 2003, the entire content of each of which is hereby incorporated by reference in its entirety.

FIELD OF THE INVENTION

This invention relates to methods for carrying out multiple binding reactions between bio-molecules in an array-format and more specifically to such systems and methods using biosensors and more specifically using optical detection methods such as surface plasmon resonance (SPR).

BACKGROUND OF THE INVENTION

In the new era of genomics, proteomics and bio-informatics, a vast number of proteins, new drug targets and small molecules are being investigated intensively and in high-throughput fashion. Although the full mapping of the human genome is done, genomics cannot provide a complete understanding of cellular processes which involve functional interactions between proteins and other molecules as well. Therefore, proteomics may be considered as a cutting-edge area of research today, bridging genomics and cell function.

Current technological methods for analyzing a large number of functional interactions between bio-molecules (especially proteins) include well-plate based screening systems (e.g., ELISA), cell-based assays, soluble reactants screening (e.g., radio immunoassays) and solid-phase assays (e.g., DNA-chips). Today, there is an obvious lack of high throughput technology which enables real-time, label-free monitoring of kinetics of multiple bio-molecular interactions (especially proteins).

The major current limitation in developing such solid-phase based-assays stems from the complexity and variability of proteins. Proteins, in contrast to DNA molecules which are used in producing DNA-chips, are less stable, and generally must be kept hydrated and in an active structure and conformation. Also, proteins are very sensitive to chemical and physical changes (e.g., temperature). Finally, with regard to solid-phase kinetic studies, the amount or capacity of an immobilized protein must be known in order to perform an accurate, full kinetic study.

As used herein, the term "biosensor" refers to combination of a receptor surface for molecular recognition and a transducer for generating signals indicative of binding to the surface.

Various related optical methods can be used to measure kinetic binding interactions between bio-molecules. These include, among others, Surface Plasmon Resonance (SPR), total internal reflection fluorescence (TIRF) and evanescent wave elipsometry. It is known in the art to use biosensors and mainly SPR for such purpose. A kinetic binding reaction involves a first molecular species referred to herein as "the probe". The probe is adsorbed to the sensor surface, and a solution containing a second molecular species, referred to herein as "the target" is then allowed to flow over the probe molecules adsorbed onto the sensor surface. As is known in the art and in commercially available devices, a standard kinetic binding interaction measurement can be described by the following procedure:

(1) Chemical activation of solid-phase surface with a chemical activator (e.g., EDC/NHS); (2) Immobilization of a 'probe' molecule on a chemically-activated surface; (3) Washing and blocking of un-occupied activated groups with a blocker such as 1M ethanolamine; (4) Addition of one concentration of a 'target' molecule; (5) Washing and regeneration of the 'probe' with appropriate regenerating chemicals (e.g., 50 mM NaOH, 0.05% SDS); (6) Addition of another concentration of 'target'; (7) Repeat stages 4-6, at least five times, each time with a different 'target' concentration.

In one aspect of this invention, the invention provides a method, referred to herein as "One-Shot Kinetics" (OSK). for obtaining one or more kinetic parameters of a binding reaction As shown below, this method allows carrying out a plurality of binding reactions without the need of the regeneration stage which is known to be harmful to the 'probe'.

In general, any binding event between probe and target molecules can alter an SPR detection parameter which is than is used to monitor the binding reaction. The change in the detection parameter over time is used to determine a characteristic of the binding reaction, such as an association or dissociation constant rates as well as affinity. It is known to use surface Plasmon resonance (SPR) as the method of detection. SPR devices and methods are very sensitive to changes in an optical property of a probe layer and have proven to be useful in detecting changes in an optical property of a probe layer generated by relatively small stimuli.

An SPR probe layer may be configured as a multi-analyte "microarray" in which at each of a plurality of discrete regions, "microspots" on the sensor surface a probe material for interaction with a target material is adsorbed. Berger et al., describes a method for preparing a probe array and for presenting targets to the probe array so as to monitor the binding of the targets to the probes ("Surface Plasmon Resonance Multi-Sensing", Anal. Chem. Vol. 70, February 1998, pp 703-706,.

PCT publication WO 02/055993, discloses the use of electrostatic fields and chemical cross-linking for binding probes to a sensor surface.

SUMMARY OF THE INVENTION

The present invention provides a system and method for determining kinetic parameters of one or more binding reactions between one or more probes and one or more targets. The probes and targets may be, for example, peptides, proteins, nucleic acids or polysaccharides. The probes and targets may be of the same species. For example, both of them may be proteins. Alternatively, the probes and targets may be of different species. For example, the probes may be nucleic acids, while the targets are proteins.

The system of the invention uses any detection method suitable for use in biosensors. More specifically, it uses a detection method based on an evanescent wave phenomenon such as surface plasmon resonance (SPR), critical angle refractometry, total internal reflection fluorescence (TIRF), total internal reflection phosphorescence, total internal reflection light scattering, evanescent wave elipsometry or Brewster angle reflectometry. The detection method makes use of a surface that allows a plurality of binding reactions to be monitored simultaneously. The method comprises adsorbing the probes to the sensor surface at different locations on the surface, for example by means of micro-fluidic methods using a chemical surface activator, or using a localized electric field. Each target is then presented to its respective probe adsorbed to the surface. The binding reactions between each pair of probe and target are monitored simultaneously.

In its first aspect, the present invention provides a system and method for determination of the kinetic parameters of a binding reaction, referred to herein as "One-Shot Kinetics" (OSK). This method allows carrying out a plurality of binding reactions without the need of the regeneration stage and without the need of repeated experiments which is known to be harmful to the 'probe'. In this preferred embodiment of the method of the invention, a single probe species is adsorbed to microspots on a surface such as an SPR surface under a plurality of conditions, for example at different concentrations or pH, in order to obtain different probe densities. Some conditions may be repeated in order to obtain density duplicates. A single target species is then presented to the microspots at a plurality of concentrations. A plurality of probe density and target concentration combinations is thus obtained. The pluralities of reactions are monitored simultaneously and signals indicative of the binding reactions are obtained and analyzed so as to produce a kinetic analysis of the binding. The kinetic analysis may comprise of, for example, calculating an association constant or a dissociation constant or affinity constant for the binding of the probe to the target.

In its second aspect, the invention provides a method, referred to herein as "array-screening", for simultaneously monitoring a plurality of binding reactions between a plurality of probes and one or more targets so as to obtain analysis of many binding reactions. In one embodiment of this aspect of the invention, a specific probe species is adsorbed to the surface at different one of a plurality of microspots so that each probe in each microspot may be selected independently of the probes on the other microspots. A target species is then presented to the probe in each microspot. Binding of the targets to the probes in the plurality of microspots is monitored simultaneously and signals indicative of the binding reactions are analyzed so as to produce analysis of the binding. The analysis may comprise of, for example, determining the existence of a detectable interaction at each microspot or calculating an equilibrium constant for the binding of the probe to the target at each microspot or determining the kinetics of binding.

The probes may be localized at different locations on the surface, for example, by means of micro-fluidic methods. The location on the surface may be activated, for example by using a chemical activator, or by applying an electric field, or by exposure to light (photo-activation). In order to achieve, localization, it is known to form a chemical thin layer covering a specific region of the surface, frequently referred as a binding layer. The binding layer may include different functional groups that are chemically activated, either by contact with chemical reagents, by applying an electric field, or by exposure to light (photo-activation).

Activation by an electric field may be carried out in two principal ways: (A) inducing an electrochemical reaction (reduction or oxidation) of functional groups in the binding layer. (B) applying an electric field so as to attract charged bio-molecules to the surface, and thus enhance the immobilization reaction; thus forming a higher local concentration of the probe molecules at the surface.

The most common binding layers for protein immobilization contain carboxylic groups. These carboxylic groups are activated by exposing the surface to accepted chemical activators, generally a mixture of EDC (1-ethyl-3-(3-dimethylaminopropyl) carbodiimide) and NHS (N-hydroxysuccinimide)) in an aqueous solution. As a result, active NHS esters are formed. When the activated surface is contacted with a protein solution, the NHS esters react efficiently with nucleophilic groups on the protein backbone, mainly with amino groups to form stable amide bonds. Thus, covalent immobilization of proteins is achieved. Other methods for chemical activation include attachment of a molecule that exhibits a high affinity to the candidate for immobilization, e.g. attachment of avidin or an avidin derivative for immobilization of biotin-labeled molecules.

The invention also provides a method for preparing a probe array for use in the method of the invention for monitoring binding reactions. Thus, in its first aspect, the invention provides a method for determining one or more kinetic parameters of binding between a first binding member and a second binding member comprising:
(a) adsorbing the first binding member to a surface at a plurality of microspots;
(b) presenting the second binding member to the first binding member at each of the microspots, there being a plurality of combinations of first binding member surface density and second binding member concentration among the plurality of microspots;
(c) simultaneously obtaining data indicative of a binding reaction between the first and second binding members at each of the plurality of microspots by a biosensor detection method; and
(d) processing the data so as to obtain one or more kinetic parameters of binding between the first and second binding members.

In its second aspect, the invention provides a method for localizing a molecular species at each of two or more microspots on a surface, comprising, for each of one or more localization regions:
(a) activating the surface in the localization region;
(b) for each of one or more microspots in the localization region, adsorbing a molecular species to the microspot; and
(c) optionally deactivating the localization region.

In its third aspect, the invention provides a probe array produced by the method of the invention.

In its fourth aspect the invention provides a system for simultaneously monitoring a plurality of binding reactions between one or more probe species and one or more target species comprising
(a) A surface;
(b) An applicator capable of applying probe species to microspots on the surface so as to allow the probe species to be adsorbed to the microspot, the applicator being further capable of presenting a target to each probe species adsorbed to the surface;
(c) A photosurface receiving light reflected from the surface and generating signals indicative of the binding of the targets to the probes; and
(d) A processor configured to receive the signals generated by the photosurface and to analyze the signals so as to produce a kinetic analysis of the binding.

BRIEF DESCRIPTION OF FIGURES

In order to understand the invention and to see how it may be carried out in practice, a preferred embodiment will now be described by way of non-limiting example only, with reference to the following accompanying drawings, in which:

FIG. 6A is a graphical representation of binding curves of Anti IgG1 to six antibody probes;

FIG. 6B is a graphical representation of binding curves of Anti IgG2b to six antibody probes;

FIG. 6C is a graphical representation of binding curves of Anti IgA to six antibody probes;

FIG. 6D is a graphical representation of binding curves of Anti IgG1 to six antibody probes;

FIG. 6E is a graphical representation of binding curves of Anti IgG3 to six antibody probes;

DETAILED DESCRIPTION OF EXEMPLARY EMBODIMENTS

Figure 1A:
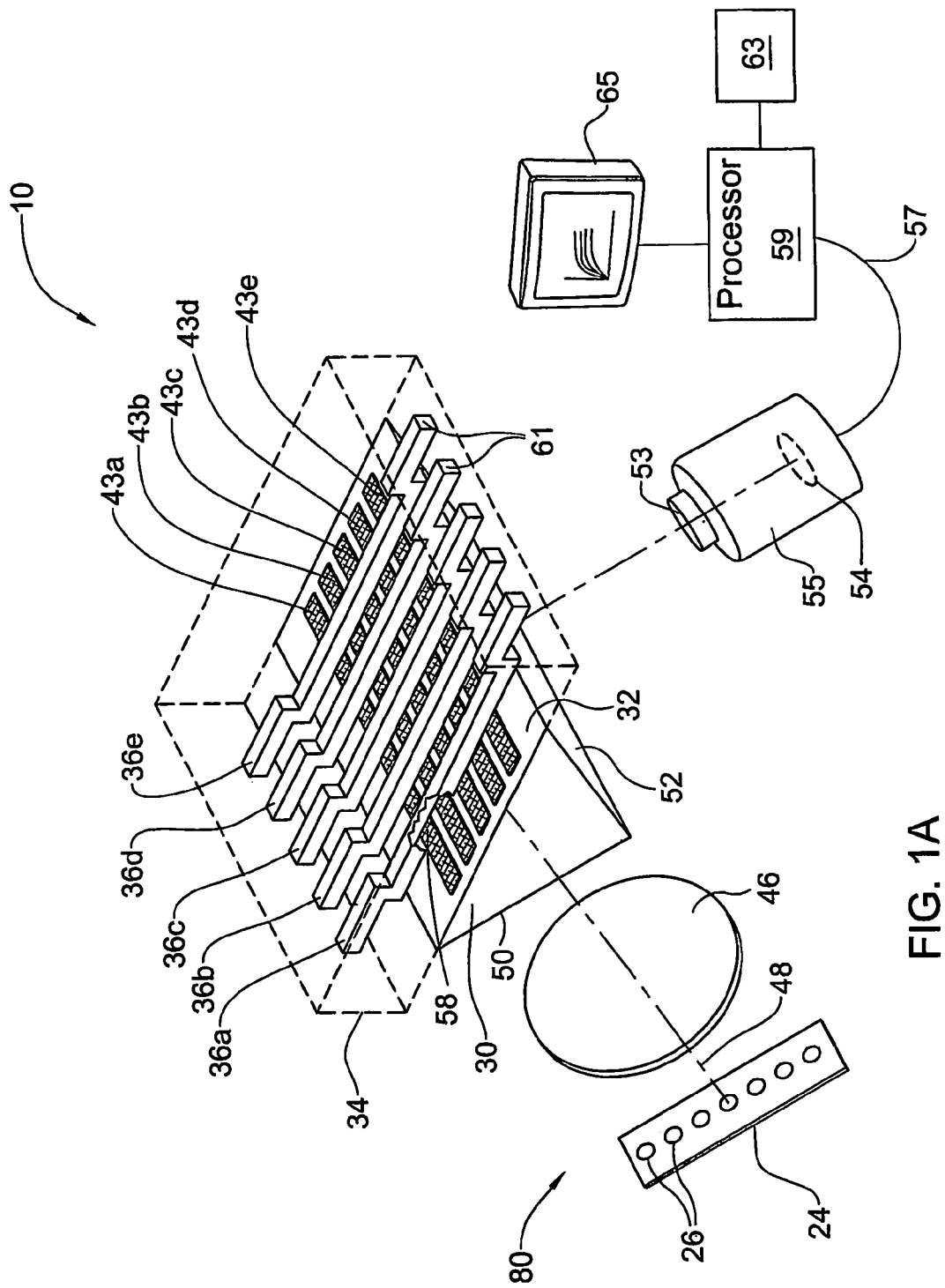
FIG. 1A is a representation of a system for performing multiple binding reactions in accordance with an embodiment of the present subject matter.
Figure 1B:
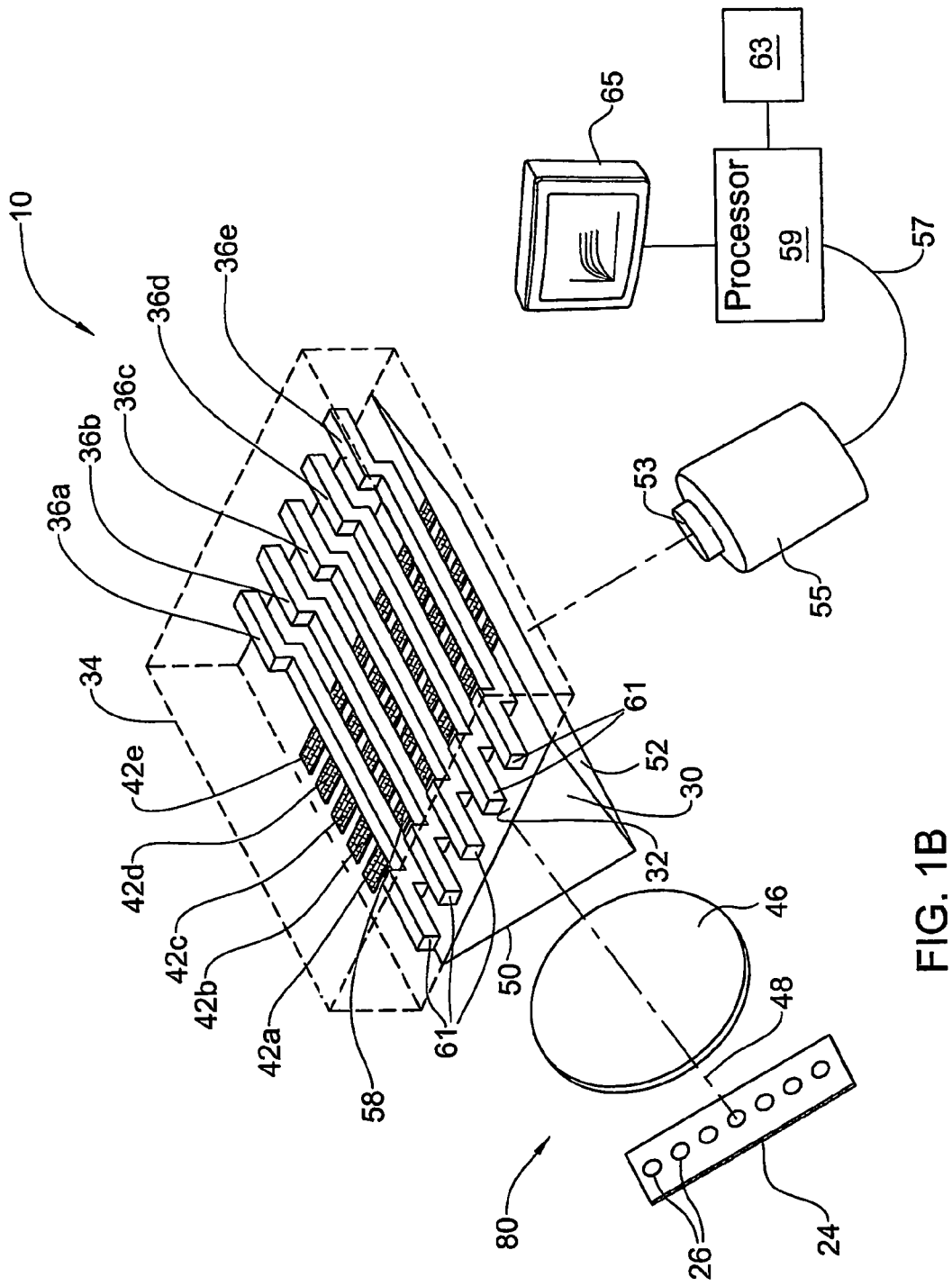
FIG. 1B is another representation of a system for performing multiple binding reactions in accordance with an embodiment of the present subject matter.

FIGS. 1a and 1b schematically show a system 10 for simultaneously carrying out multiple binding reactions in accordance with one embodiment of this aspect of the invention. The system 10 includes an SPR device 80 comprising an array 24 of light sources 26 and a prism 30 having a sensor surface 32. The light sources 26 provide light at a wavelength appropriate for SPR applications as is known in the art. The light array 24 is positioned at the focal plane of an optical system schematically represented by a lens 46 having an optical axis 48. Lens 46 collects and collimates light from each light source 26 into a beam of parallel light rays and directs the collimated light so that it is incident on an "input" prism surface 50 of prism 30. Light directed by collimator 46 that is incident on input surface 50 enters prism 30 and is incident on sensor surface 32.

All light incidents on the sensor surface 32 from a given light source 26 is incident on the sensor surface at substantially a same incident angle and light from different light sources 26 is incident on the sensor surface at different incident angles. The angle at which light from a given light source 26 is incident on sensor 26 on sensor surface 32 is determined by the position of the given light source along the axis of the array 24, the focal length of the lens 46 and the index of refraction of the material from which prism 30 is formed. The SPR device 80 may include a "displacement plate" (not shown) formed from a transparent material that is positioned between light source array 24 and prism 30. The angular orientation of displacement plate is set so that the normal to the displacement plate is oriented at a desired angle with respect to the optic axis 48.

Light incident on sensor surface 32 that is reflected from the surface exits prism 30 through an output prism surface 52 and is collected and imaged by a camera 55 having a lens 53 and a two dimensional photosurface 54 such as a CCD. A polarizer (not shown) is positioned between the array 24 and the prism 30 or preferably between the prism 30 and the camera 55. The polarizer linearly polarizes light received by photosurface 54 so that relative to sensor surface 32 it has substantially only a p component of polarization.

The camera 55 outputs signals 57 that are indicative of images formed on the photosurface 54. The signals 57 are input to a processor 59 having a memory 63 for storing signals 57. The processor 59 is configured to analyze the signals as described below. Any of the signals 57 or results of the analysis performed by the processor may be displayed on an associated display screen 65.

The system 10 includes a flow cell 34 having m microchannels 36 for flowing liquid across and in contact with the sensor surface 32. In the device 80, m=5 microchannels 36a to 36e are shown. This is by way of example only, and the method of the invention may be carried out using flow cell having any number m of microchannels. The outer form of flow cell 34 is shown in ghost lines and details of internal features, such as microchannels 36, of the flow cell are shown in solid lines for clarity of presentation. Each microchannel 36 has at one end an inlet (not visible in the perspectives shown in FIGS. 1a and 1b) and, at its other end, an outlet 61 through which fluid flowing in the microchannel exits the microchannel. Each of the inlets is adapted to be independently connected to a suitable pumping apparatus (not shown) in order to introduce a fluid independently into each of the m microchannels 36.

In the system 10, the flow cell 34 is mountable onto the SPR surface in two orientations. One of the two orientations is shown in FIG. 1a and is referred to herein as "the probe orientation". The second orientation, shown in FIG. 1b is referred to herein as the "target orientation". In each of the two orientations, the microchannels are perpendicular to the microchannels in the other orientation. Each microchannel 36 is open on a side of the microchannel facing sensor surface 32 so that fluid flowing in the microchannel, in either orientation, contacts the SPR surface in a rectangular region. In the probe orientation shown in FIG. 1a, fluid flowing in a microchannel contacts the sensor surface at a respective rectangular region 42 referred to herein as the microchannel's "probe region" (see FIG. 1b). In the target orientation shown in FIG. 1b, fluid flowing in a microchannel contacts the sensor surface at a respective rectangular region 43 referred to herein as the microchannel's "target region" (see FIG. 1a). The probe regions and the target regions are thus perpendicular to each other. Regions of some microchannels 36 in the system 10 in FIGS. 1a and 1b are cut away to show microspots 58 formed at the crossover regions of the probe regions and the target regions.

Figure 2:
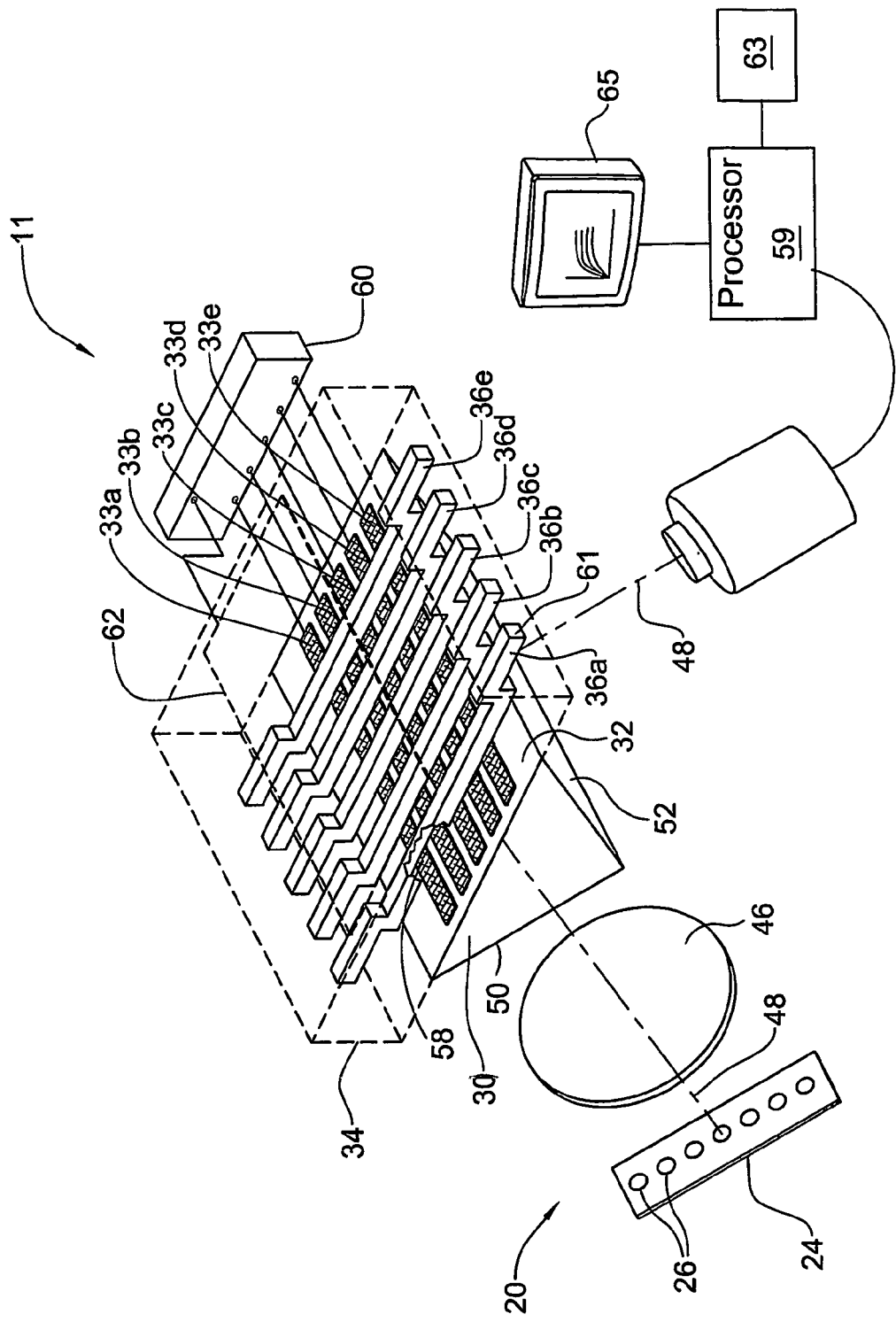
FIG. 2 is a representation of a system for performing multiple binding reactions in accordance with another embodiment of the present subject matter.

FIG. 2 schematically shows a system 11 for simultaneously carrying out multiple binding assays in accordance with another embodiment of this aspect of the invention. The system 11 includes an SPR device 20 having several components in common with the SPR device 80 shown in FIGS. 1A and 1B, and similar components are indicated with the same reference numeral in both figures. In particular, the SPR device 80 includes an optical system comprising an array 24 of light sources 26, a prism 30 having a sensor surface 32, a lens 46 having an optical axis 48, and a two dimensional photosurface 54 such as a CCD. A suitable SPR conductor (not shown) is formed on the sensor surface.

The system 11 includes a flow cell 34 having m microchannels 36 for flowing liquid across and in contact with the sensor surface 32. In the device 80, m=5 microchannels 36a to 36e are shown. This is by way of example only, and the method of the invention may be carried out using a flow cell having any number m of microchannels. The outer form of flow cell 34 is shown in ghost lines and details of internal features, such as microchannels 36, of the flow cell are shown in solid lines for clarity of presentation. Each microchannel 36 has at one end an inlet (not visible in the perspectives shown in FIGS. 1a and 1b) and, at its other end, an outlet 61 through which fluid flowing in the microchannel exits the microchannel. Each of the inlets is adapted to be independently connected to a suitable pumping apparatus (not shown) in order to introduce a fluid independently into each of the m microchannels 36.

The SPR device 20 has n strip electrodes 33. The n strip electrodes are used to create n independently activatable regions. While n=5 strip electrodes 33a to 33b are shown in FIG. 2, this is by way of example only and the method of the invention may be carried out with an SPR device having any number of strip electrodes.

In the system 11, the flow cell 34 is mounted onto prism 30 so that the m microchannels are perpendicular to the n strip-electrodes 33. Each microchannel 36 is open on a side of the microchannel facing sensor surface 32 so that fluid flowing in the microchannel contacts each strip electrode 33 at a microspot 58 located at the crossover region of the microchannel with the strip electrode. In an SPR device having m microchannels and n strip electrodes, a total of m×n microspots are formed at eh crossover regions of the m microchannels with the n strip electrodes. Regions of some microchannels 36 in SPR device 20 in FIG. 2 are cut away to show microspots 58.

Each strip electrode 33 is independently connected to a power supply 60. Power supply 60 is controllable to independently bring each strip electrode 33 to a voltage relative to a reference electrode 62 connected to the power supply so as to generate an electric field having a component perpendicular to the sensor surface 32. The electric field passes through the lumen of the microchannels 36 at the crossover region of the microchannels with the strip electrode.

Figure 3A:
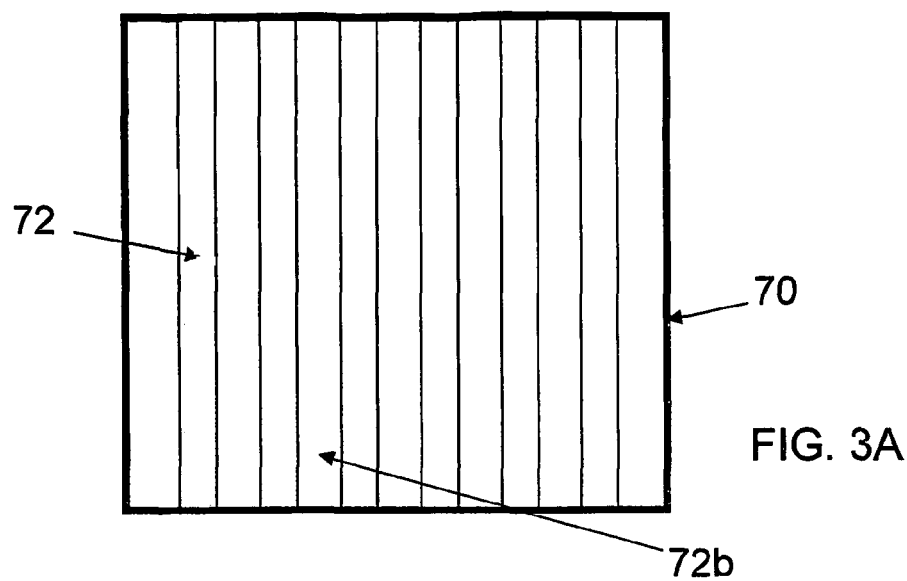
FIG. 3A is a representation of a method for preparing a probe array in accordance with an embodiment of the present subject matter.
Figure 3B:
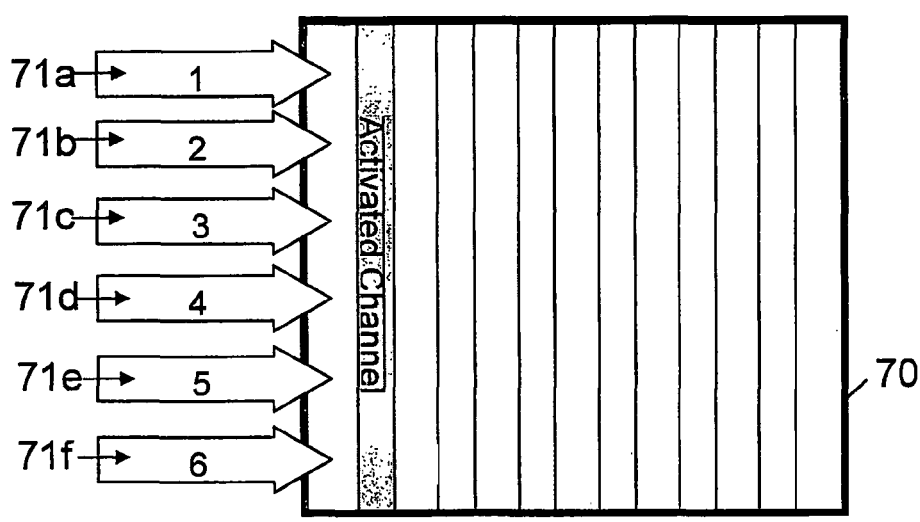
FIG. 3B is a representation of a method for preparing a probe array in accordance with another embodiment of the present subject matter.
Figure 3C:
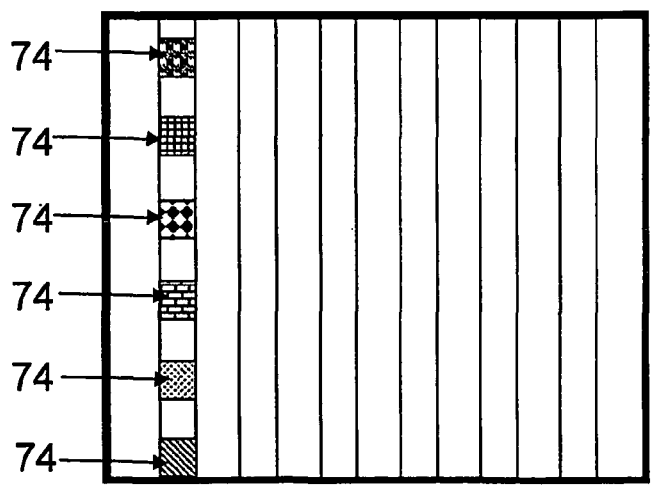
FIG. 3C is a representation of a method for preparing a probe array in accordance with an additional embodiment of the present subject matter.

FIGS. 3A, 3B, 3C, and 3D schematically show methods for preparing a probe array on a surface 70 in accordance with one embodiment of the method of the invention. In FIG. 3a, a first surface region 72a on the surface 70 is activated. Activation of a surface region allows probe molecules to be adsorbed to the surface region. One or more probe species 71 are then adsorbed to the activated first surface region 72 (FIG. 3b) at distinct microspots in the first surface region 72. FIG. 3b schematically shows the application of 6 probe species 71a to 71f to the activated first surface region 72a. This is by way of example only and the method of the invention may be carried out with any number of probe species 71 being adsorbed to the first surface region 72. This produces the probe array shown in FIG. 3c, in which each probe species is adsorbed to a different microspot 74. FIG. 3c shows 6 microspots 74a to 74f. The probe species may all be different or some of the probe species may be the same possibly at different concentrations.

Figure 3D:
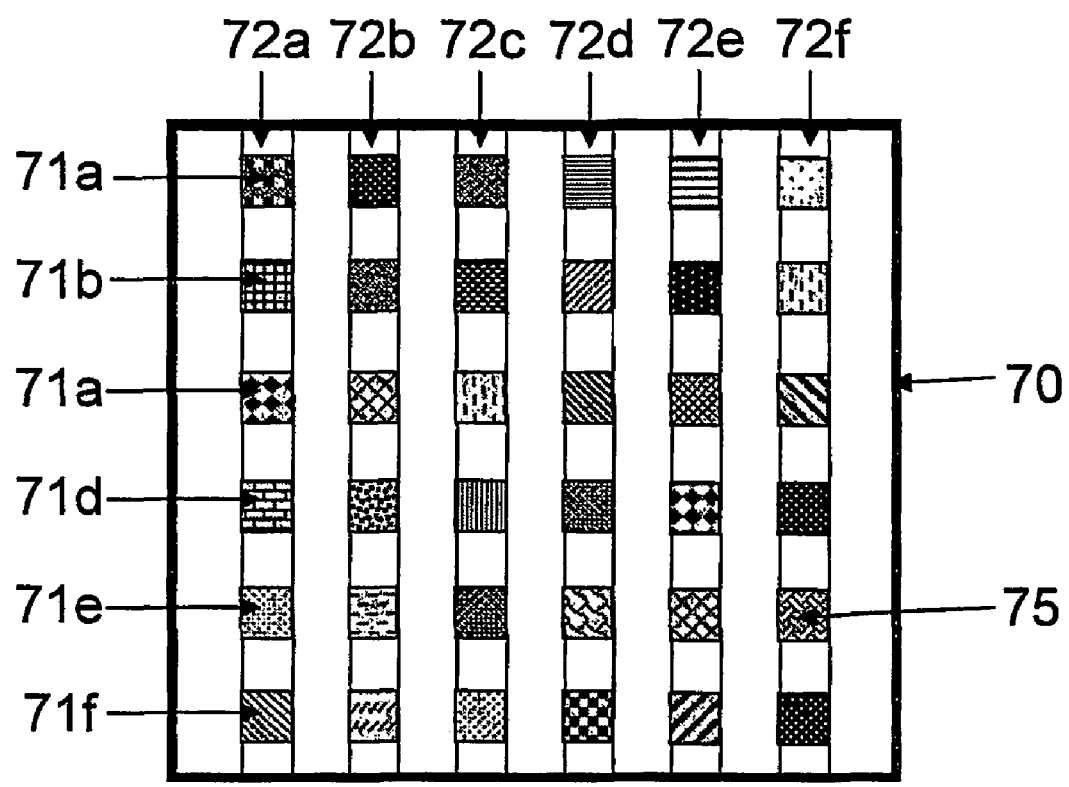
FIG. 3D is a representation of a method for preparing a probe array in accordance with a further embodiment of the present subject matter.

The first surface region is now deactivated and a second surface region 72b is activated. One or more probe species are then adsorbed to distinct microspots on the second surface region 72b, as explained above for the first surface region 72a. The process is repeated, each time activating a different one of the surface regions 72 until probe species have been adsorbed to microspots on each of the surface regions 72. This produces the probe array shown in FIG. 3d in which a plurality of probe species is adsorbed to microspots 75. In FIG. 3d, 6 surface regions 72a to 72f are shown. This is by way of example only, and the method of the invention may be carried out with any number of surface regions 72. In the example shown in FIG. 3d, on each of the 6 surface regions 72, 6 probe species were adsorbed. This produces the array of 36 microspots shown in FIG. 3d. The probe species adsorbed on different surface regions may be different, so that up to 36 different probe species may be adsorbed onto the surface 70.

After the probe array on the surface 70 has been prepared, for each surface region, a target species may presented to the probe species adsorbed to the microspots.

The method of preparing a probe array on a surface shown in FIGS. 3A, 3B, 3C, and 3D will now be demonstrated with reference to the system 10 of FIGS. 1A and 1B. In this example, $m^2$ probe species are to be adsorbed to the SPR surface at the $m^2$ microspots 58 ($m^2$=25 in the SPR device 80 of FIGS. 1A and 1B) located at the $m^2$ crossover regions of the m probe regions with the m target regions. To prepare an appropriate microarray of the $m^2$ probes on the probe regions, the flow cell 34 is first placed in one orientation (FIG. 1*b*) and buffer or water is first pumped through the first microchannels 36 in order to clean and prepare the first surface region 43*a*. Flow of buffer or water through the first microchannel 36*a* is then stopped a solution of a chemical surface activator is then made to flow through the first microchannel 36*a* in order to activate the first surface region 43*a*. The first surface region is now activated.

The flow cell is now rotated 90° to bring it from the target orientation shown in FIG. 1*b* to the probe orientation shown in FIG. 1*a*. An appropriate solution comprising a probe species is pumped through each of the m microchannels 36. The m probe species may all be different, or some may be the same probe species, possibly at different concentrations. As a result of the activation of the first surface region 43*a*, each probe species is adsorbed to the first surface region 43*a* and is not adsorbed by the other m−1 surface regions 43*b* 43*e*. Each of the probe species is thereby immobilized at a different one of the m microspots 58 located at the m crossover regions of the m probe regions 42 with the first surface region 54*a*. The probes are substantially prevented from immobilizing at the m×(m−1) microspots 58 located at the crossover regions of the m probe regions 42 with the m−1 other surface regions 43*b*-43*e*.

During immobilization of the probes, the process of immobilization and the quantities of probe proteins immobilized at each microspot 58 are monitored by performing an SPR angular scan of the sensor surface 64, as is known in the art. The signals 57 generated by the CCD 54 responsive to light from each light source 26 reflected at each microspot 58 on the first surface region 43*a* during adsorption of the probes are input to the processor 59. The processor 59 is configured to analyze the signals so as to determine an SPR parameter for the microspot. The SPR parameter may be, for example, the SPR resonance angle, resonance wavelength, or the reflectance and phase changes that characterize a surface Plasmon resonance. The processor is further configured to analyze the SPR parameter so as to monitor accumulation of the probe immobilized at the microspot. Signals 57 from microspots of the other m−1 surface regions and from regions of the probe surface that are not crossover regions are analyzed by the processor to correct and normalize signals from crossover regions of the first surface region.

After termination of the flow of the probe solutions in the microchannels, the flow cell is rotated 90° back to the target orientation (FIG. 1*b*) and a solution containing a surface activator blocker is made to flow through the microchannels 36 to prevent further binding to the first surface region.

The above-described process is repeated for each of the other remaining m−1 surface regions 43*b*-43*a* with m probe solutions, until a probe species has been immobilized at each of as many as $m^2$ different microspots 58 located at the $m^2$ crossover regions of the m probe regions and the m surface regions. Each surface region 43 may thus be activated individually. As used herein, the term "activatable region" is used to refer to a region that can, when activated, bind one or more probe species. Thus, with the method of the invention, a probe microarray comprising as many as $m^2$ different probe species may be formed on the SPR surface of the SPR device 80.

Following preparation of the probe microarray, a solution containing a target species is made to flow in each of the m microchannels 36 in the flow cell with the flow cell in the target orientation. The m target species may all be different, or some of the target species may be the same, possibly at different concentrations. Thus, for each of the m target solutions, the target is presented to each of the m probe species in the m microspots 58 located at the m crossover regions of the target's target region with the m probe regions. The signals 57 provided by the CCD 54 responsive to light from the light sources reflected from each of the $m^2$ microspots 58 during flow of the target molecules in the microchannels are input to the processor 59. The processor 59 is configured to analyze these signals in order to monitor the binding of target to probe at each microspot. A total of as many as $m^2$ binding reactions can thus be monitored simultaneously involving as many as $m^2$ different probe species and as many as m different target species. As known in the art, reference surface must be used and be subtracted from any signal obtained from 'active spot'. In one aspect of this invention, and as a novel outcome of the method, the surface between the spots, termed "inter-spot" is used as a reference surface.

The method of preparing a probe array on a surface shown in FIGS. 3A, 3B, 3C, and 3D will now be demonstrated with reference to the system 11 of FIG. 2. In this example, m×n probe species are to be adsorbed to the SPR surface that at the m×n microspots 58 (m×n =25 in the system 11 of FIG. 2) located at the m×n crossover regions of the m microchannels 36 with the n strip electrodes 33. To prepare an appropriate microarray of the m×n probes on the strip electrodes 33, buffer or water is first pumped through the microchannels 36 to clean and prepare the strip electrodes for immobilization of the probe molecules at the microspots 58. Flow of buffer or water through the m microchannels is then stopped and the first strip electrode 33*a* is now activated as explained above. The remaining strip electrodes are all brought to a potential with respect to the reference electrode 62 having a polarity opposite to that of the first electrode. An appropriate solution comprising a probe species is pumped through each of the m microchannels 36. The m probe species may all be different, or some may be the same probe species, possibly at different concentrations. As a result of the activation of the first strip electrode 33*a* and the charge on the m probe species in the microchannels, each probe species is adsorbed to the first strip electrode 33*a* and is not adsorbed by the other n−1 strip electrodes 33*b*-33*e*. Each of the probe species is thereby immobilized at a different one of the m microspots 58 located at the m crossover regions of the m microchannels with the first strip electrode 33*a*. The probes are substantially prevented from immobilizing at the m×(n−1) microspots 58 located at the crossover regions of the m microchannels with the n−1 other strip electrodes 33b-33e.

During immobilization of the probes, the process of immobilization and the quantities of probe proteins immobilized at each microspot 58 are monitored by performing an SPR angular scan of the sensor surface 64, as is known in the art. The signals 57 generated by the CCD 54 responsive to light from each light source 26 reflected at each microspot 58 on the first strip electrode 33a during adsorption of the probes are input to the processor 59. The processor 59 is configured to analyze the signals so as to determine an SPR parameter for the microspot. The processor is further configured to analyze the SPR parameter so as to monitor accumulation of the probe immobilized at the microspot. Signals from microspots of the other n−1 strip electrodes 33b-33e and from regions of the probe surface that are not crossover regions are analyzed by the processor to correct and normalize signals from crossover regions of the first target region.

After termination of the flow of the probe solutions in the microchannels, buffer or water is again made to flow through the microchannels 36 to eliminate unbound probe proteins.

The above-described process is repeated for each of the other remaining n−1 strip electrodes 33b-33e with m probe solutions, until a probe species has been immobilized at each of as many as m×n different microspots 58 located at the m×n crossover regions of the m microchannels 36 and the n strip electrodes 33. Thus, with the method of the invention, a probe microarray comprising as many as m×n different probe species may be formed on the SPR surface of the SPR device 20.

Following preparation of the probe microarray, a solution containing a target species is made to flow in each of the m microchannels 36. The m target species may all be different, or some of the target species may be the same, possibly at different concentrations. Thus, for each of the m target solutions, the target is presented to each of the n probe species in the n microspots 58 located at the n crossover regions of the target's microchannel with the n strip electrodes. The signals 57 provided by the CCD 54 responsive to light from the light sources reflected from each of the $m^2$ microspots 58 during flow of the target molecules in the microchannels are input to the processor 59. The processor 59 is configured to analyze these signals in order to monitor the binding of target to probe at each microspot. A total of as many as m×n binding reactions can thus be monitored simultaneously involving as many as m×n different probe species and as many as m different target species. In a preferred embodiment, a region of the surface, referred to as "an interspot" is used as a reference surface to provide a reference signal.

Figure 4A:
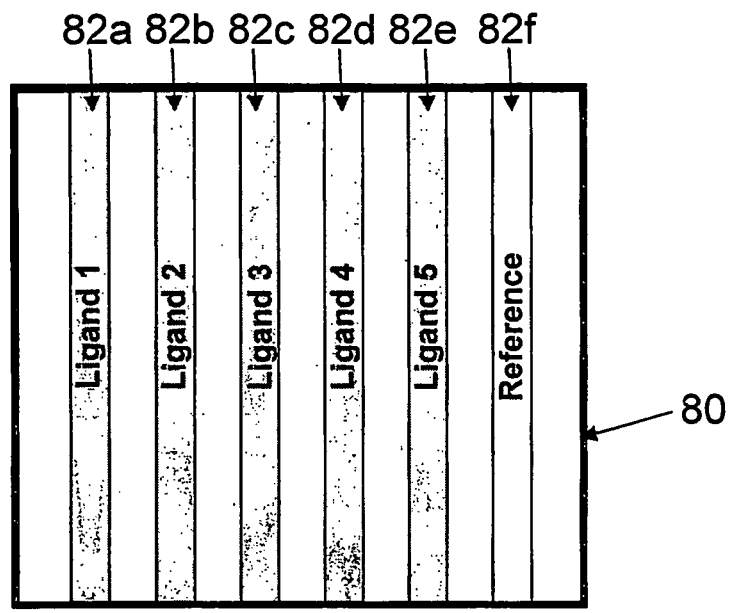
FIG. 4A is a representation of a method for preparing a probe array in accordance with yet another embodiment of the present subject matter.
Figure 4B:
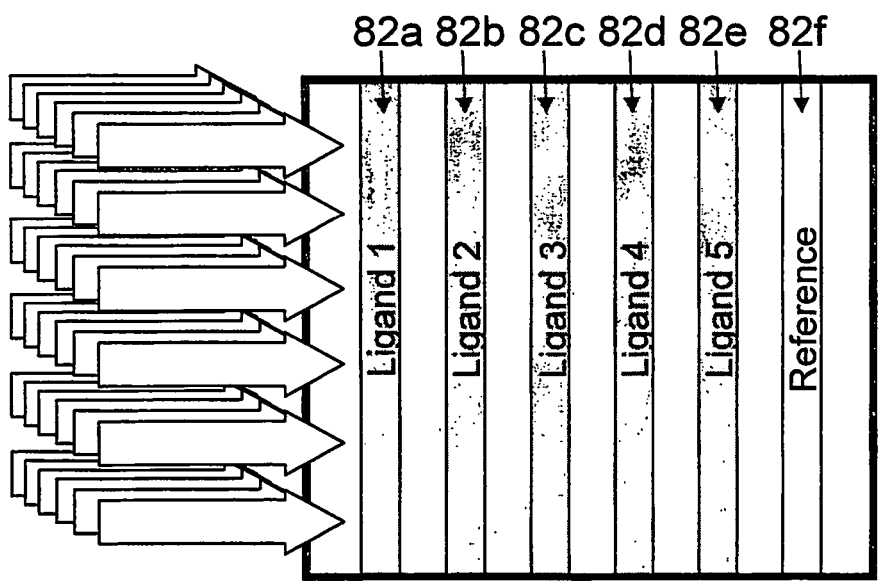
FIG. 4B is a representation of a method for preparing a probe array in accordance with an additional embodiment of the present subject matter.
Figure 5A:
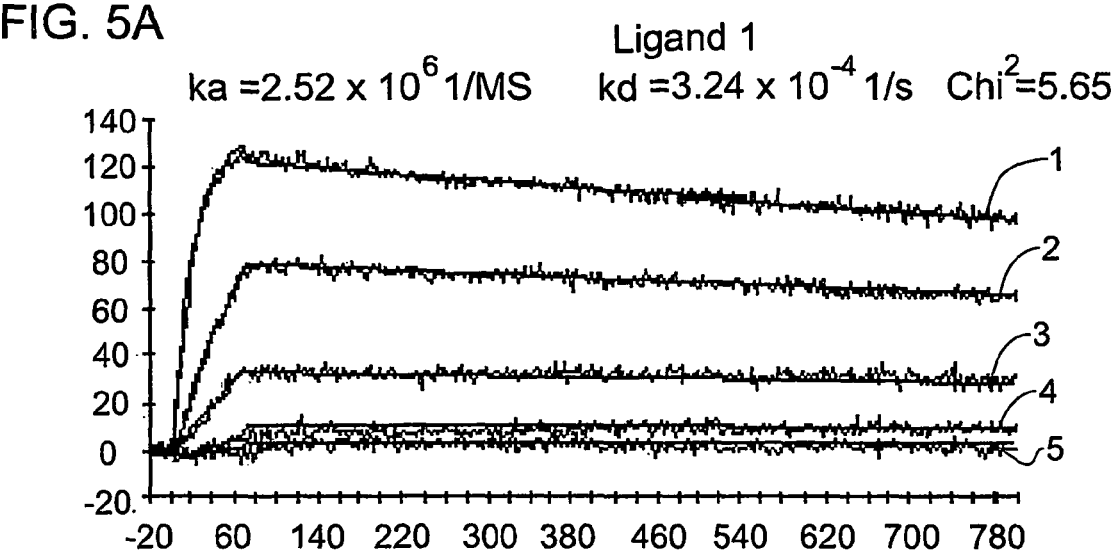
FIG. 5A is a graphical representation of binding curves of IL-4 to anti-IL-4 antibody at Ligand1 of a probe array obtained by a method of the present subject matter.
Figure 5B:
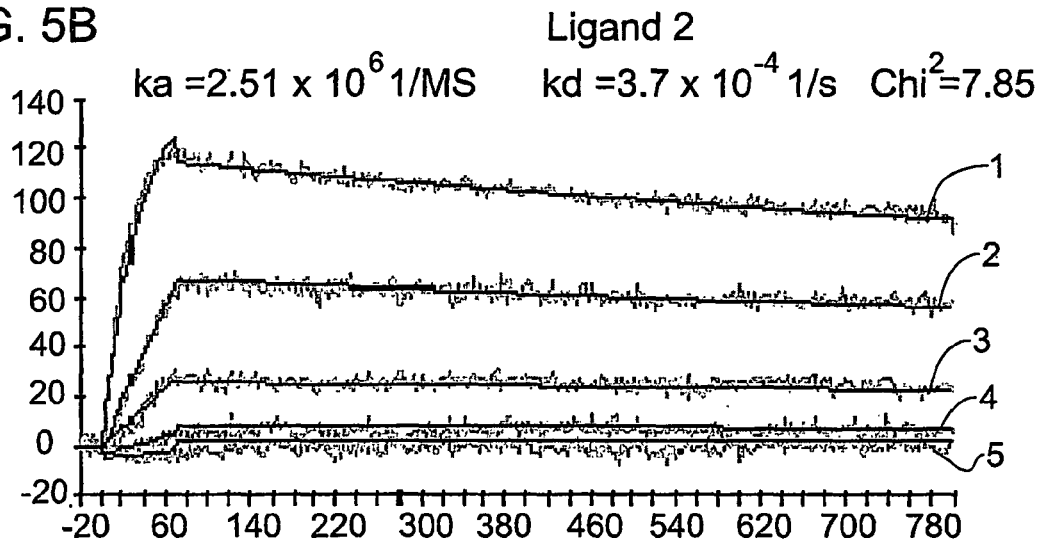
FIG. 5B is a graphical representation of binding curves of IL-4 to anti-IL-4 antibody at Ligand 2 of a probe array obtained by a method of the present subject matter.
Figure 5C:
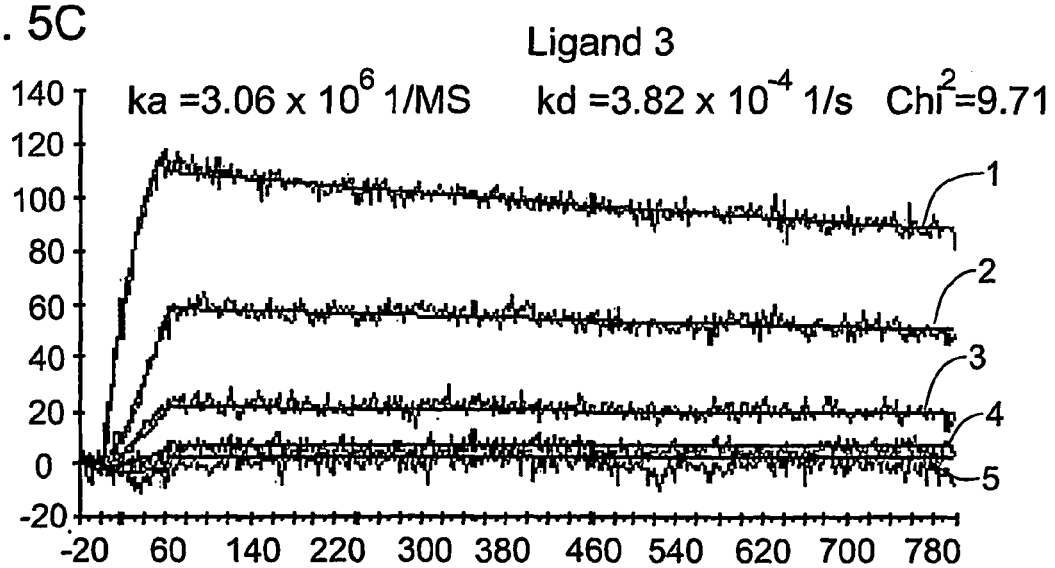
FIG. 5C is a graphical representation of bindings curve of IL-4 to anti-IL-4 antibody at Ligand 3 of a probe array obtained by a method of the present subject matter.
Figure 5D:
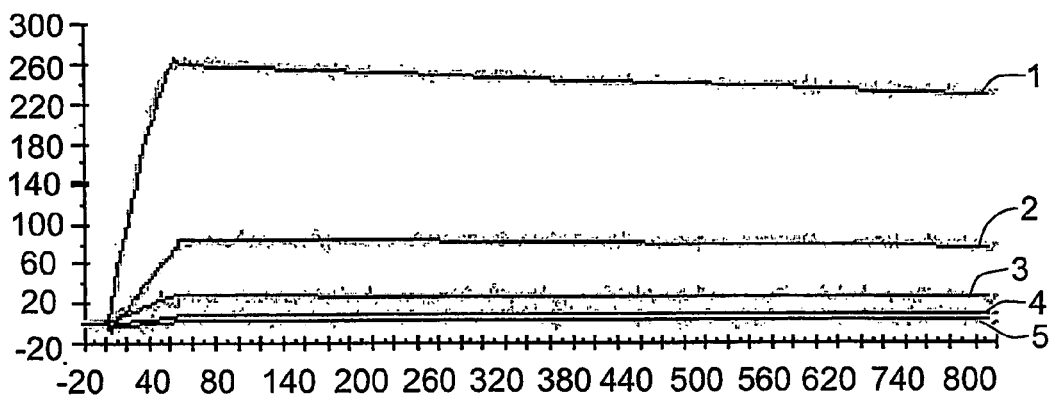
FIG. 5D is a graphical representation of binding curves of IL-4 to anti-IL-4 antibody at Ligand 4 of a probe array obtained by a method of the present subject matter.
Figure 5E:
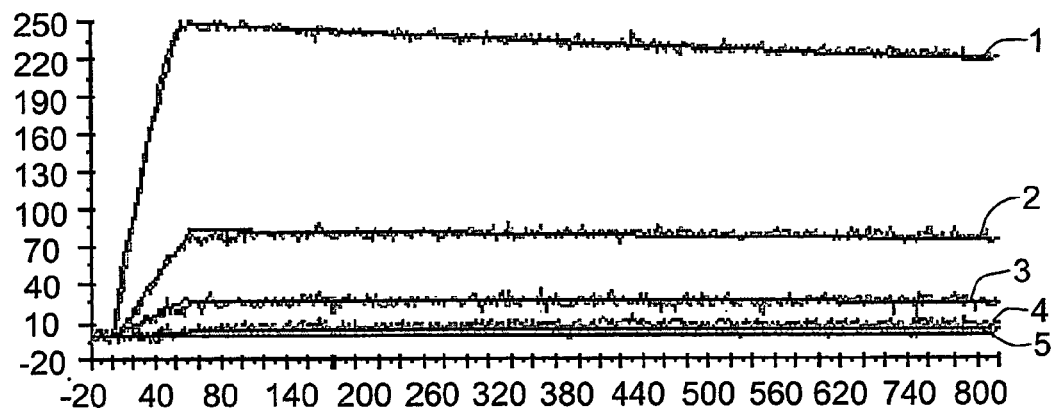
FIG. 5E is a graphical representation of binding curves of IL-4 to anti-IL-4 antibody at Ligand 5 of a probe array obtained by a method of the present subject matter.
Figure 5F:
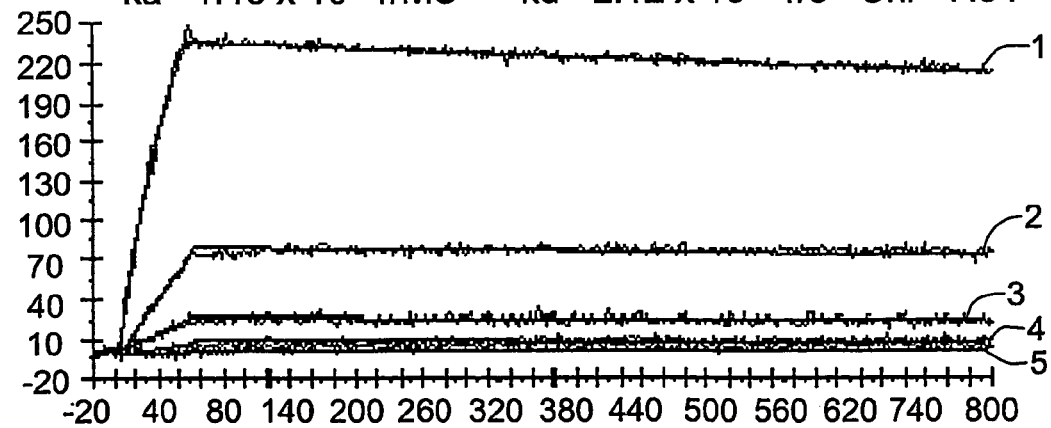
FIG. 5F is a graphical representation of binding curves of aIL-4 to anti-IL-4 antibody at Ligand 6 of a probe array obtained by a method of the present subject matter.
Figure 7A:
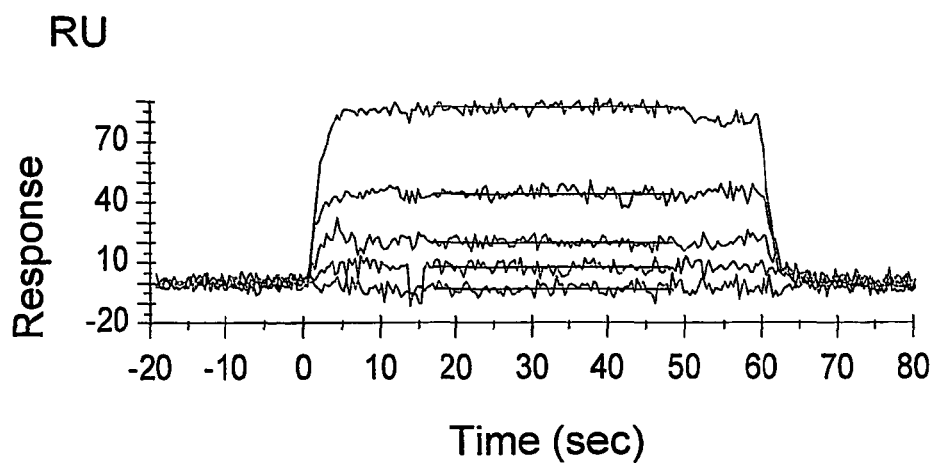
FIG. 7A is a graphical representation of binding curves of various compound targets to six CYP450 enzyme probes.
Figure 7B:
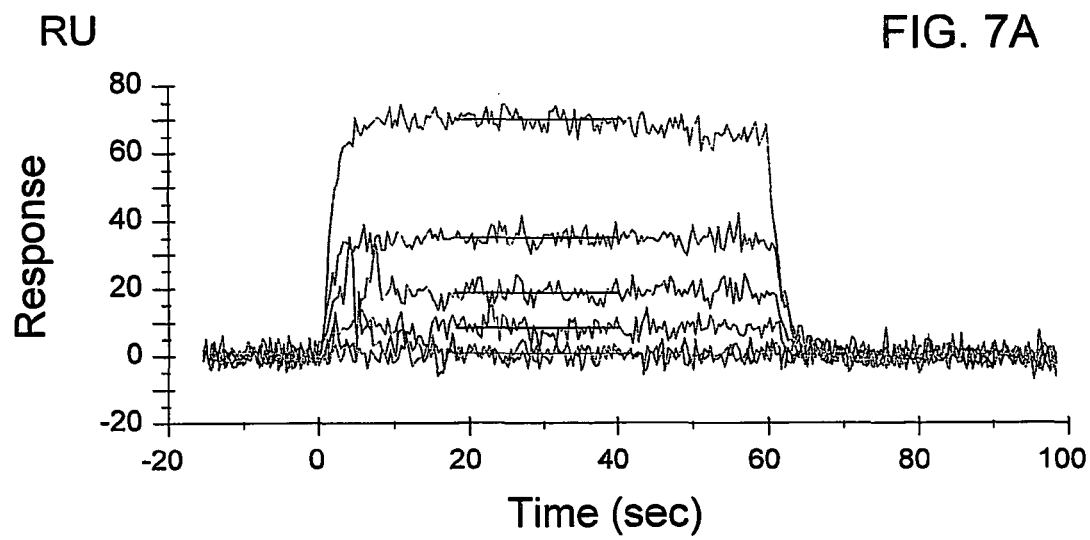
FIG. 7B is graphical representation of additional binding curves of various compound targets to six CYP450 enzyme probes.
Figure 7C:
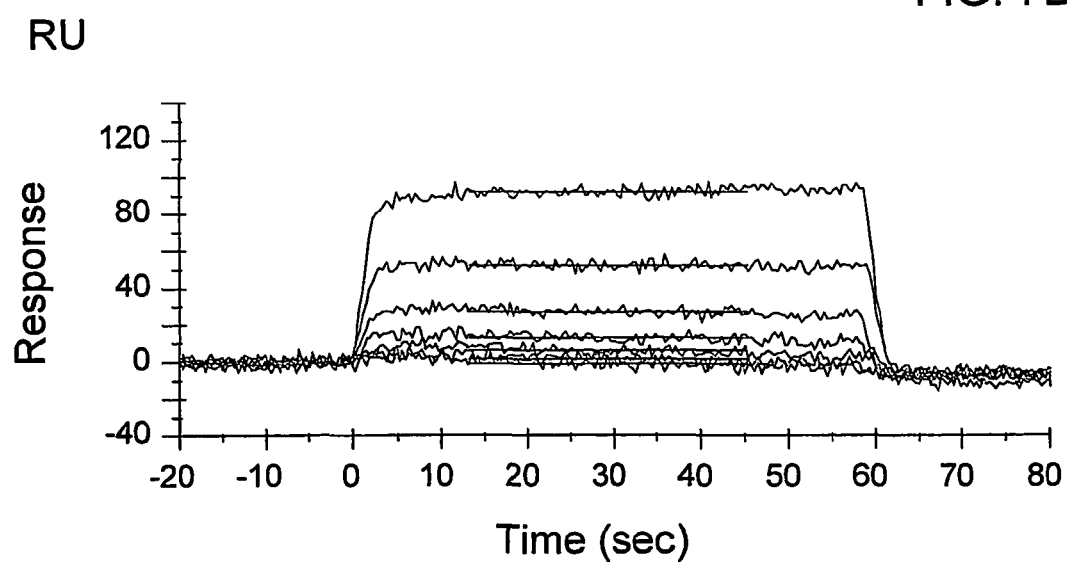
FIG. 7C is a graphical representation of several more binding curves of various compound targets to six CYP450 enzyme probes.
Figure 7D:
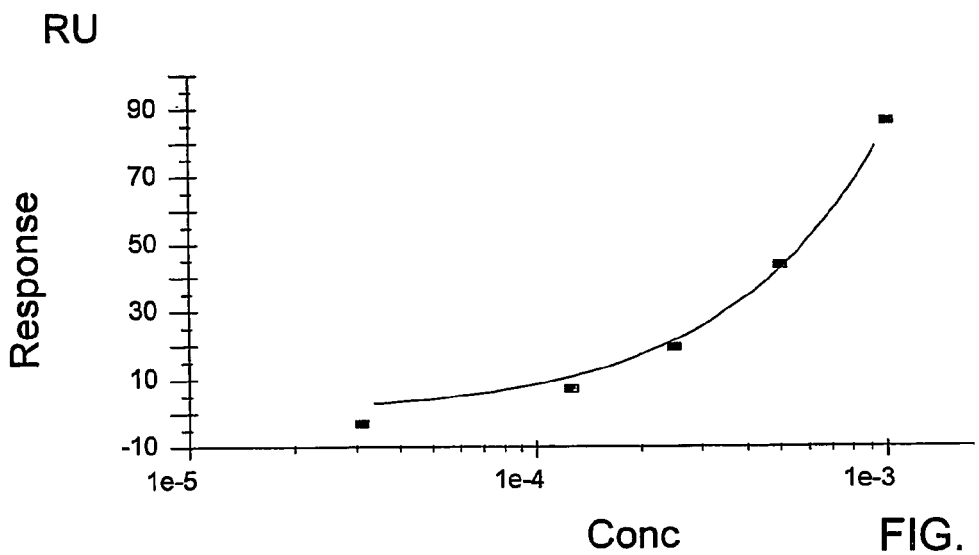
FIG. 7D is a graphical representation of response verse concentration for five Cytochrome-P450 (CYP) enzyme probes (3A4, 2C19, 1A2, 2C9 and 2D6)
Figure 7E:
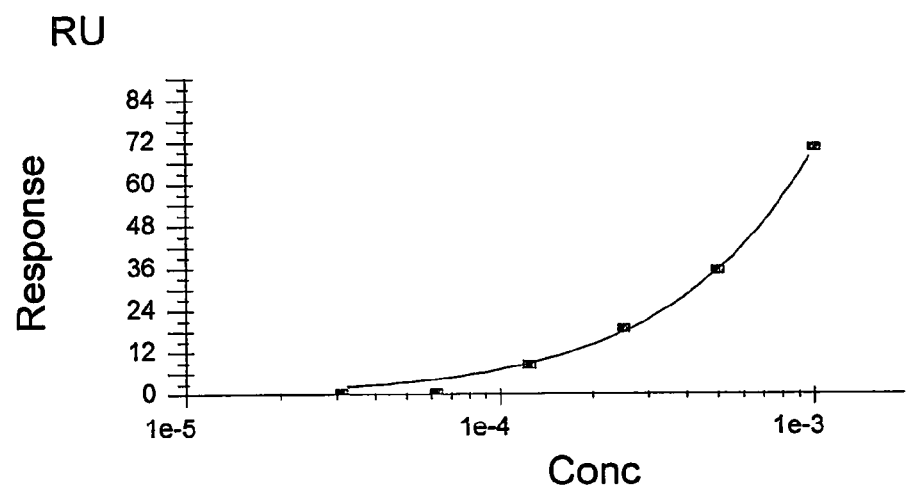
FIG. 7E is another graphical representation of response verse concentration for five Cytochrome-P450 (CYP) enzyme probes (3A4, 2C19, 1A2, 2C9 and 2D6)
Figure 7F:
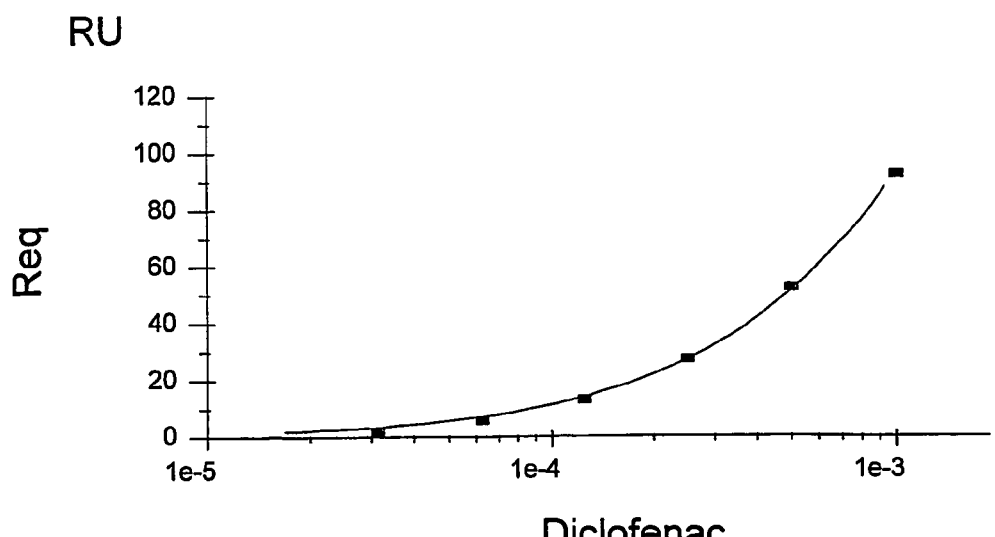
FIG. 7F is an additional graphical representation for five Cytochrome-P450 (CYP) enzyme probes (3A4, 2C19, 1A2, 2C9 and 2D6).

FIGS. 4A and 4B show a method for preparing a probe array on a surface 80 in accordance with another embodiment of the method of the invention (termed "OSK" or "one-shot kinetics"). This embodiment may be used when it is desired to perform a binding assay involving one probe species and one target species at different combinations of probe and target concentrations. In this embodiment, m probe regions 82 are simultaneously activated. 6 probe regions 82a to 82f are shown in FIG. 4a. This is by way of example only, and the method may be carried out with any number of probe regions. The m probe regions 82 are activated and the probe is adsorbed onto the probe regions 82. A different probe concentration is adsorbed onto each probe region. One of the probe regions 82f may be used as a reference region upon which no probe is adsorbed.

As depicted in FIG. 4b, n concentrations of the target are then presented to the probe array (designated analytes 1-6). Each concentration is presented to a different microspot on each of the probe regions. The reaction assay thus consists of all of the m×n combinations of the probe and target concentrations.

The method of performing a binding assay shown in FIGS. 4A and 4B will now be demonstrated with reference to the system 10 of FIGS. 1A and 1B. This embodiment is used when it is desired to perform a binding assay involving one probe species and one target species at different combinations of probe and target concentrations. The probe species is applied to each of the m probe regions at a different concentration, and the target is applied to each of the m target regions at a different concentration. To prepare this microarray, the flow cell 34 is first placed in the probe orientation (FIG. 1a) and buffer or water is first pumped through the m microchannels 36 in order to clean and prepare the m probe regions 42. Flow of buffer or water through the m microchannels 36 is then stopped and any residual buffer or water in the flow system is drained away. A solution of a chemical surface activator is then made to flow through the m microchannels 36 in order to activate the m probe regions 42. The surface activator may be, for example, EDC/NHS. The m probe regions are now activated.

An appropriate solution comprising the probe is pumped through each of the m microchannels 36. In this embodiment, the probe is present in each of the different microchannels at a different concentration. As a result of the activation of the target regions 42, probe molecules in each microchannel are adsorbed to the n microspots 58 in contact with the microchannel.

During immobilization of the probes, the process of immobilization and the quantities of probe proteins immobilized at each microspot 58 are monitored by performing an SPR angular scan of the sensor surface 64, as is known in the art. The signals 57 generated by the CCD 54 responsive to light from each light source 26 reflected at each probe region 42 during adsorption of the probe are input to the processor 59. The processor 59 is configured to analyze the signals so as to determine an SPR parameter for each probe region 42. The processor is further configured to analyze the SPR parameter so as to monitor accumulation of the probe immobilized on each probe region 42. Signals 57 regions of the SPR surface not in a probe region are analyzed by the processor to correct and normalize signals from the probe regions.

After termination of the flow of the probe solutions in the microchannels, a solution containing a surface activator blocker is made to flow through the microchannels 36 to prevent further binding of molecules to the SPR surface. The surface activator blocker may be, for example, ethanolamine.

The flow cell is now rotated 90° from the probe orientation to the target orientation (FIG. 1b). A solution containing the target species is made to flow in each of the m microchannels 36 of the flow cell. In this embodiment, the target is present in the different microchannels at a different concentration. Thus, for each of the m target solutions, the target is presented to each of the m probe concentrations species in the m microspots 58 located at the m crossover regions of the target solution with the m probe regions. The signals 57 provided by the CCD 54 responsive to light from the light sources reflected from each of the $m^2$ microspots 58 during flow of the target molecules in the microchannels are input to the processor 59. The processor 59 is configured to analyze these signals in order to monitor the binding of target to probe at each microspot. In this embodiment, a total of $m^2$ binding reactions are thus monitored simultaneously involving as many as $m^2$ different combinations of probe concentration and target concentration. This allows the collection of kinetic data on the binding of the target to the probe for kinetic analysis in a single binding assay, without the need to regenerate the surface at any time. This is in contrast to prior art methods in which reactions are performed sequentially, each time with a different combination of probe and target concentrations which requires regeneration of the surface between successive binding reactions.

The method of performing a binding assay shown in FIGS. 4A and 4B will now be demonstrated with reference to the system 11 of FIG. 2. The probe species is applied to each of the m probe regions at a different concentration, and the target is applied to each of the m target regions at a different concentration. To prepare this microarray, the flow cell 34 is positioned as shown in FIG. 2 with the m microchannels 36 perpendicular to the n strip electrodes 33. Buffer or water is first pumped through the microchannels 36 to clean and prepare the SPR surface in contact with the microchannels Flow of buffer or water through the m microchannels is then stopped and the n strip electrodes 33 are now activated as explained above. An appropriate solution comprising the probe is pumped through each of the m microchannels 36. In this embodiment, the probe is present in each of the different microchannels at a different concentration. As a result of the activation of the strip electrodes 33 and the charge on the probe in the microchannels, probe molecules are adsorbed to the strip electrodes 33. Probe molecules are thereby immobilized at a different one of the n microspots 58 located at the n crossover regions of the microchannel with the n strip electrodes 33.

During immobilization of the probes, the process of immobilization and the quantities of probe proteins immobilized at each microspot 58 are monitored by performing an SPR angular scan of the sensor surface 64, as is known in the art. The signals 57 generated by the CCD 54 responsive to light from each light source 26 reflected at each microspot 58 on the first strip electrode 33a during adsorption of the probes are input to the processor 59. The processor 59 is configured to analyze the signals so as to determine an SPR parameter for the microspot. The processor is further configured to analyze the SPR parameter so as to monitor accumulation of the probe immobilized at each microspot. Signals 57 from regions of the probe surface that are not microspots are analyzed by the processor to correct and normalize signals from of the microspots.

After termination of the flow of the probe solutions in the microchannels, buffer or water is again made to flow through the microchannels 36 to eliminate unbound probe proteins.

The flow cell 34 now removed from the SPR surface and a second flow cell (not shown) having n microchannels is positioned on the SPR surface with a microchannel overlaying each of the n strip electrodes 33. In the case that m=n, the flow cell 34 may also be used as the second flow cells by rotting it 90° from the orientation shown in FIG. 2 to an orientation (not shown) in which the microchannels 36 overlay the strip electrodes 33. A solution containing the target is made to flow in each of the n microchannels. In this embodiment, the target is present in the different microchannels at a different concentration. Thus, for each of the n target solutions, the target is presented to each of the m probe concentrations in the m microspots 58 located at the m crossover regions of the targets microchannel with the m probe regions. The signals 57 provided by the CCD 54 responsive to light from the light sources reflected from each of the n×m microspots 58 during flow of the target molecules in the microchannels are input to the processor 59. The processor 59 is configured to analyze these signals in order to monitor the binding of target to probe at each microspot. This allows collection of kinetic data on the binding of the target to the probe for kinetic analysis in a single binding assay, without the need to regenerate the surface at any time. This is in contrast to prior art methods in which reactions are performed sequentially, each time with a different combination of probe and target concentrations which requires regeneration of the surface between successive binding reactions.

EXAMPLES

Example 1

A binding assay was carried out using the system 10 shown in FIGS. 1A and 1B. Anti-IL-4 antibody (αIL-4) was used as a probe in this experiment and was localized on the SPR surface in each of six rectangular probe regions 42 (see FIGS. 1A and 1B), as explained above in the description of the system 10. The probe regions were labeled (a) to (f). The density of the antibody, in "response units" (RU), in each of the 6 probe regions is given in Table 1.

TABLE 1

| Probe region | Target (αIl-4) concentration ($pg/mm^2$) (RU) |
| --- | --- |
| (a) | 530 |
| (b) | 315 |
| (c) | 346 |
| (d) | 360 |
| (e) | 334 |
| (f) | 355 |

IL-4 was used as the target in this experiment was presented to the αIL-4 in each of five target regions 43 (see FIGS. 1A and 1B), as explained above. The target regions were numbered 1 to 5. The concentration of IL-4 in each target region is given in Table 2.

TABLE 2

| Probe Localization Site | Target (IL-4) concentration (nM) |
| --- | --- |
| (1) | 26.7 |
| (2) | 8.89 |
| (3) | 2.96 |

TABLE 2-continued

| Probe Localization Site | Target (IL-4) concentration (nM) |
|---|---|
| (4) | 0.98 |
| (5) | 0.33 |

The binding assay thus involved 30 binding reactions that were performed simultaneously. Binding of IL-4 to αIL-4 in the 30 microspots was monitored simultaneously as described above. The results of the binding are shown in FIGS. 5A, 5B, 5C, 5D, 5E and 5F. Each graph in FIGS. 5A, 5B, 5C, 5D, 5E and 5F shows binding of IL-4 to αIL-4 in the probe region indicated in the graph. Each of the 5 curves in the graph shows the results of the binding of IL-4 to αIL-4 in the microspot located at the intersection of the probe region of the graph and the target region specified for each curve. At the times indicated by the arrow in each graph, unbound IL-4 was rinsed away, and the dissociation of bound IL-4 from αIL-4 in the 30 microspots was monitored simultaneously by the method of the invention. The processor 63 was configured to analyze the curves in each graph to obtain the association constant (Ka) and the dissociation constant (Kd) of the binding of Il-4 to αIL-4 at the antibody concentration of the graph. The Ka and Kd of each graph are shown in each of the graphs in FIGS. 5A, 5B, 5C, 5D, 5E and 5F. From these, the affinity constant (KD) can be derived, as is known in the art.

Example 2

Binding between 6 antibody probes (αIgG1, αIgG2b, αIgA, αIgG2a and αIgG3) to 5 antigen targets (IgG1, IgG1, IgG2a, IgG2b and IgG3) was studied using the system 10 of FIGS. 1A and 1B. The concentrations used of the probes and targets are given in Tables 3 and 4, respectively. The binding curves obtained are shown in FIGS. 6A 6B, 6C, 6D and 6E, and the binding response of each of the 30 binding reactions is shown in Table 5.

TABLE 3

| Probe | Probe region | Probe concentrations (pg/mm$^2$) (RU) |
|---|---|---|
| Anti mouse IgG2a | a | 3410 |
| Anti mouse IgG2b | b | 4170 |

TABLE 3-continued

| Probe | Probe region | Probe concentrations (pg/mm$^2$) (RU) |
|---|---|---|
| Anti mouse IgG1 | c | 3970 |
| Anti mouse IgG3 | d | 3500 |
| Anti mouse IgA | e | 3770 |
| Reference surface | f | — |

TABLE 4

| Target | Target concentrations(μg/ml) |
|---|---|
| IgG1 (anti IL-2) | 2.5 |
| IgG1 (anti IL-4) | 2.5 |
| IgG2a | 5 |
| IgG2b | 5 |
| IgG3 | 5 |
| Mouse IgG | 5 |

The Binding Responses to Different Antibody Subclasses (in Response Units)

TABLE 5

| Ligand Analyte | Anti mouse IgG2a | Anti mouse IgG2b | Anti mouse IgG1 | Anti mouse IgG3 | Anti mouse IgA |
|---|---|---|---|---|---|
| IgG1 (anti IL-2) | 21 | 42 | 44 | — | — |
| IgG1 (anti IL-4) | 23 | — | 45 | — | — |
| IgG2a | 90 | — | — | — | — |
| IgG2b | — | 241 | — | — | — |
| IgG3 | — | — | — | 97 | — |
| IgG polyclonal | 122 | 67 | 44 | 30 | — |

Example 3

The binding of five Cytochrome-P450 (CYP) enzyme probes (3A4, 2C19, 1A2, 2C9 and 2D6) with 6 different targets (Ketoconazole, Nifedipine, Dextromethorphan, Diclofenac, Dulfaphenazole and Propranolol) was carried out using the system 10 of FIGS. 1A and B. The targets were presented at concentrations of 1,000, 500, 250, 125, 62.5, 31.25, 15.5, and 7.8 μM. The affinity constant, KD was determined for each reaction. The results are shown in FIGS. 7A, 7B, 7C, 7D, 7E and 7F, and Table 6.

TABLE 6

Affinity constants (KD in [M]) determined for binding of various compounds to five CYP enzymes.

| | CYP-P450 | | | | |
|---|---|---|---|---|---|
| | 3A4 | 2C19 | 1A2 | 2C9 | 2D6 |
| Ketoconazole | 2.59E−05 | 5.21E−05 | 1.33E−03 | 7.65E−05 | 2.10E−04 |
| Nifedipine | 1.84E−03 | 2.24E−03 | 5.81E−02 | 1.42E−03 | 4.37E−03 |
| Dexomethorphan | 1.26E−02 | 7.90E−03 | — | 2.83E−02 | 6.04E−02 |
| Diclofenac | 4.47E−04 | 7.17E−04 | 1.42E−02 | 1.66E−04 | 6.81E−04 |
| Sulfaphenazole | 1.65E−01 | 1.14E−02 | 1.15E−03 | 2.06E−03 | 7.11E−02 |
| Propranolol | 7.53E−02 | 6.59E−03 | 8.73E−04 | 5.13E−03 | 5.22E−03 |

Example 4

Table 7 shows immobilization of Rabbit IgG and Goat IgG probes on 36 independent microspots prepared by the method shown in FIGS. 3A, 3B, 3C and 3D, using the system 10 of FIGS. 1A and 1B. Each probe region was sequentially activated and six alternate probes of Rabbit IgG and Goat IgG were adsorbed onto the activated probe region. This resulted in the immobilization of 36 alternate probes in the 36 microspots (6 in each surface region), as shown in Table 7.

TABLE 7

|   | 1 | 2 | 3 | 4 | 5 | 6 |
|---|---|---|---|---|---|---|
| 1 | Goat IgG 543 RU | Rabbit IgG 1640 RU | Goat IgG 963 RU | Rabbit IgG 1950 RU | Goat IgG 1050 RU | Rabbit IgG 1420 RU |
| 2 | Rabbit IgG 1620 RU | Goat IgG 1060 RU | Rabbit IgG 1800 RU | Goat IgG 1020 RU | Rabbit IgG 1320 RU | Goat IgG 1060 RU |
| 3 | Goat IgG 525 RU | Rabbit IgG 1870 RU | Goat IgG 1200 RU | Rabbit IgG 1960 RU | Goat IgG 1300 RU | Rabbit IgG 1430 RU |
| 4 | Rabbit IgG 1730 RU | Goat IgG 1300 RU | Rabbit IgG 2070 RU | Goat IgG 1240 RU | Rabbit IgG 1540 RU | Goat IgG 1360 RU |
| 5 | Goat IgG 608 RU | Rabbit IgG 1660 RU | Goat IgG 1200 RU | Rabbit IgG 2160 RU | Goat IgG 1340 RU | Rabbit IgG 1730 RU |
| 6 | Rabbit IgG 1680 RU | Goat IgG 1080 RU | Rabbit IgG 1910 RU | Goat IgG 1120 RU | Rabbit IgG 1530 RU | Goat IgG 1110 RU |

Mouse anti-rabbit and mouse anti-goat antibody targets were then presented to the probe array. Table 8 shows the target binding responses. Each of the 36 independently selected probes in the probe array reacts with its corresponding target allowing 36 different and independent interactions to be performed and monitored simultaneously (in a "checker board" pattern).

TABLE 8

| 1 | 2 | 3 | 4 | 5 | 6 |
|---|---|---|---|---|---|
| Anti Rabbit (0 RU) | Anti Rabbit (348 RU) | Anti Rabbit (2 RU) | Anti Rabbit (431 RU) | Anti Rabbit (1 RU) | Anti Rabbit (291 RU) |
| Anti Goat (308 RU) | Anti Goat (5 RU) | Anti Goat (553 RU) | Anti Goat (0 RU) | (Anti Goat (584 RU) | Anti Goat (0 RU) |
| Anti Rabbit (354 RU) | Anti Rabbit (0 RU) | Anti Rabbit (415 RU) | Anti Rabbit (0 RU) | Anti Rabbit (262 RU) | Anti Rabbit (0 RU) |
| Anti Goat (0 RU) | Anti Goat (573 RU) | Anti Goat (0 RU) | Anti Goat (571 RU) | (Anti Goat (1 RU) | Anti Goat (579 RU) |
| Anti Rabbit (4 RU) | Anti Rabbit (402 RU) | Anti Rabbit (1 RU) | Anti Rabbit (435 RU) | Anti Rabbit (0 RU) | Anti Rabbit (291 RU) |
| Anti Goat (299 RU) | Anti Goat (4 RU) | Anti Goat (650 RU) | Anti Goat (1 RU) | (Anti Goat (687 RU) | Anti Goat (1 RU) |
| Anti Rabbit (362 RU) | Anti Rabbit (0 RU) | Anti Rabbit (480 RU) | Anti Rabbit (0 RU) | Anti Rabbit (309 RU) | Anti Rabbit (0 RU) |
| Anti Goat (1 RU) | Anti Goat (674 RU) | Anti Goat (0 RU) | Anti Goat (660 RU) | (Anti Goat (1 RU) | Anti Goat (704 RU) |
| Anti Rabbit (0 RU) | Anti Rabbit (355 RU) | Anti Rabbit (3 RU) | Anti Rabbit (475 RU) | Anti Rabbit (1 RU) | Anti Rabbit (360 RU) |
| Anti Goat (353 RU) | Anti Goat (0 RU) | Anti Goat (642 RU) | Anti Goat (0 RU) | (Anti Goat (708 RU) | Anti Goat (0 RU) |
| Anti Rabbit (358 RU) | Anti Rabbit (0 RU) | Anti Rabbit (435 RU) | Anti Rabbit (1 RU) | Anti Rabbit (300 RU) | Anti Rabbit (0 RU) |
| Anti Goat (4 RU) | Anti Goat (580 RU) | Anti Goat (2 RU) | Anti Goat (602 RU) | Anti Goat (2 RU) | Anti Goat (595 RU) |

The invention claimed is:

1. A method for determining one or more kinetic parameters of binding between a first binding member and a second binding member comprising:

simultaneously adsorbing the first binding member to a surface at a plurality of microspots, the adsorbing comprising activating the surface of at least one microspot by presenting thereto a chemical activating substance, the activating comprising
forming a first channel around a region containing the at least one microspot,
introducing a solution containing the activating substance into the channel, and
removing excess activating solution from the channel,
adsorbing the first binding member to the at least one microspot, and deactivating the at least one microspot;
simultaneously presenting the second binding member at a plurality of concentrations to the first binding member at the plurality of microspots, there being a plurality of combinations of first binding member surface density and second binding member concentrations among the plurality of microspots;
simultaneously obtaining one or more kinetic parameters indicative of a binding reaction between the first and second binding members at each of the plurality of microspots to produce a kinetic analysis of the binding, the binding being detected by a biosensor detection method;
simultaneously obtaining reference data from a plurality of interspots, each of the interspots located at a surface between at least two or more the microspots; and processing the binding kinetic parameters and the reference data to obtain one or more kinetic parameters characteristic of the binding between the first and second binding members,
wherein the plurality of bindings carried out does not require a regeneration step.

2. The method according to claim 1, wherein the biosensor detection method is selected from the group consisting of surface plasmon resonance (SPR), critical angle refractometry, total internal fluorescence (TIRF), total internal reflection phosphorescence, total internal reflection light scattering, evanescent wave elipsometry and Brewster angle reflectometry.

3. The method according to claim 2, wherein the detection method is SPR and the data indicative of a binding reaction between the first and second binding members at each of the plurality of microspots is an SPR parameter selected from the group consisting of SPR resonance angle, resonance wavelength, reflectance changes and phase changes.

4. The method according to claim 2, wherein the one or more kinetic parameters are selected from the group consisting of an association constant $K_a$, a dissociation constant $K_d$ and an affinity constant.

5. The method according to claim 1, wherein the detection method is SPR and the data indicative of a binding reaction between the first and second binding members at each of the plurality of microspots is an SPR parameter selected from the group consisting of SPR resonance angle, resonance wavelength, reflectance changes and phase changes.

6. The method according to claim 5, wherein the one or more kinetic parameters are selected from the group consisting of an association constant $K_a$, a dissociation constant $K_d$ and an affinity constant.

7. The method according to claim 1, wherein the one or more kinetic parameters are selected from the group consisting of an association constant $K_a$, a dissociation constant $K_d$ and an affinity constant.

8. The method according to claim 1, wherein the step of adsorption to the microspot involves
forming a channel around a region containing the microspot,
introducing a solution containing the molecular species into the channel, and
removing excess solution from the channel.

9. The method according to claim 1, wherein the step of activating the surface of the microspot comprises producing an electric field over the microspot.

10. The method according to claim 1, further comprising:
deactivating portions of the surface not included in a microspot;
forming one or more second channels perpendicular to one or more of the first channels; and
for each second channel, introducing into the second channel a second binding member.

11. The method according to claim 1 further comprising obtaining reference data from a region of the surface not included in the microspots.

12. A method for localizing a molecular species at each of two or more microspots on a surface, comprising:
activating a microspot surface by:
forming a first channel around the region containing the microspot;
introducing a solution containing an activating substance into the channel; and
removing excess activating solution from the channel;
simultaneously adsorbing a molecular species to each of the two or more microspots, the adsorbing comprising
forming at least two further channels, each being perpendicular to the first channel;
simultaneously introducing a solution containing the molecular species into the channel; and
optionally deactivating the microspot,
wherein the molecular species localized on the two or more microspots may be the same in each of the microspots or different in each of the microspots, and
wherein the molecular species may be adsorbed at identical or different surface densities to each of the microspots.

13. The method according to claim 12, wherein the step of activating the microspot comprises producing an electric field over the microspot.

14. The method according to claim 12, wherein at least one of the molecular species is a first binding member and the method further comprises
forming one or more channels in a region containing the microspots;
introducing a second binding member into each of the one or more channels; and
simultaneously obtaining data indicative of a binding reaction between the first and second binding members at each of the two or more microspots by a biosensor detection method.

15. A probe array produced by the method of claim 14.
16. A probe array produced by the method of claim 12.

* * * * *